(12) United States Patent
Benedetti et al.

(10) Patent No.: US 7,691,818 B2
(45) Date of Patent: Apr. 6, 2010

(54) PEPTIDOMIMETIC INHIBITORS OF RETROVIRAL PROTEASES AND THEIR USE AS ANTIVIRALS

(75) Inventors: Fabio Benedetti, Trieste (IT); Alessandro Tossi, Farra d'Isonzo (IT); Federico Berti, Trieste (IT); Pietro Campaner, Udine (IT); Francesca Dinon, Trieste (IT)

(73) Assignee: Universita' Degli Studi Di Treiste, Trieste (IT)

( * ) Notice: Subject to any disclaimer, the term of this patent is extended or adjusted under 35 U.S.C. 154(b) by 266 days.

(21) Appl. No.: 11/629,720

(22) PCT Filed: Jun. 15, 2005

(86) PCT No.: PCT/EP2005/052770

§ 371 (c)(1),
(2), (4) Date: Dec. 15, 2006

(87) PCT Pub. No.: WO2005/123067

PCT Pub. Date: Dec. 29, 2005

(65) Prior Publication Data

US 2007/0207968 A1 Sep. 6, 2007

(30) Foreign Application Priority Data

Jun. 15, 2004 (IT) .......................... PD2004A0151

(51) Int. Cl.
*A61K 38/08* (2006.01)
*A61K 38/06* (2006.01)
*A61K 38/05* (2006.01)
*A61K 38/04* (2006.01)
*A61K 31/401* (2006.01)

(52) U.S. Cl. ............................. 514/17; 514/18; 514/19; 514/423; 530/330; 530/331; 548/530; 548/561

(58) Field of Classification Search ....................... None
See application file for complete search history.

(56) References Cited

U.S. PATENT DOCUMENTS

| 6,900,238 B1 * | 5/2005 | Wong et al. ................. 514/423 |
| 2004/0039064 A1 * | 2/2004 | Romero et al. .............. 514/651 |

OTHER PUBLICATIONS

Wlodawer, et al.: Annu Rev Biophys Biomol Struct, 27:249-284, 1998.*
International Search Report.
Cameron, C. E. et al., "Comparison of the Substrate-binding Pockets of the Rous Sarcoma Virus and Human Immunodeficiency Virus Type 1 Proteases," *J. Biol. Chem.* vol. 269, No. 16, pp. 11711-11720. XP-002347011 (ISR).
Benedetti, F. et al., "Synthesis of a Val-Pro Diaminodiol Dipeptide Isostere by Epoxyamine Cyclization," Organic Letters, vol. 6, No. 6, pp. 1017-1019. XP-002346994 (ISR).

Benedetti, F. et al., "Versatile and Stereoselective Synthesis of Diamino Diol Dipeptide Isoteres, Core Unites of Pseudopeptide HIV Protease Inhibitors," *J. Org. Chem*, 1997, vol. 62, pp. 9348-9353. XP-002346995 (ISR) (Spec, pp. 8-9 and 11).
Tossi, A. et al., "Aspartic Protease Inhibitors," European Journal of Biochemistry, 2000, vol. 267, No. 6, pp. 1715-1722. XP-002341731 (ISR).
Tossi, A. et al., "Flexible Synthesis of Symmetric and Non-symmetric HIV-1 Protease Inhibitors based on *All-S*-Diaminodiol Isosteres," Protein and Peptide Letters, 1999, vol. 6, No. 3, pp. 145-148. XP-000829954 (ISR).
Roberts, N. A. et al., "Rational Design of Peptide-Based HIV Proteinase Inhibitors," Science, vol. 248, No. 4953, pp. 358-361. XP-002024830 (ISR).
Kohl, N. et al., "Active Human Immunodeficiency virus protease is required for viral infectivity," *Proc. Natl. Acad. Sci. USA 1988*, vol. 85, pp. 4686-4690. (Spec, pp. 1 and 2).
Kramer, R. A. et al., "HTLV-III *gag* Protein is Processed in Yeast Cells by the Virus *pol*-Protease," *Science 1986*, vol. 231, pp. 1580-1584. (Spec, p. 2).
Huff, J. R., "HIV Protease: A Novel Chemotherapeutic Target for AIDS," *J. Med. Chem. 1991*, vol. 34, No. 8, pp. 2305-2314. (Spec, p. 2).
Griffiths, J. T. et al., "Different Requirements for Productive Interaction between the Active Site of HIV-1 Proteinase and Substrates Containing . . .", *J. Biochemistry 1992*, vol. 31, pp. 5193-5200. (Spec, p. 2).
Kräusslich, H.-G. et al., "Activity of purified biosynthetic proteinase of human immunodeficiency virus on natural substrates and synthetic peptides," *Proc. Natl. Acad. Sci. USA 1989*, vol. 86, pp. 807-811. (Spec, p. 2).
Graves, M.C. et al., "Identification of a Human Immunodeficiency Virus-1 Protease Cleavage Site Within the 66,000 Dalton Subunit of Reverse Transcriptase," *Biochem. Biophys. Res. Commun. 1990*, vol. 168, No. 1, pp. 30-36. (Spec, p. 2).
Wlodawer, A., Erickson, J.S., "Structure-Based Inhibitors of HIV-I Protease," *Ann. Rev. Buichem. 1993*, vol. 62, pp. 543-585. (Spec, p. 2).
Martin, J.A. et al., "5 Inhibitors of HIV Proteinase," *Progr. in Med. Chem. 1995*, vol. 32, pp. 239-287. (Spec, p. 2).
Chen, C.A. et al., "Drug Design with a New Transition State Analog of thr Hydrated Carbonyl: Silicon-based inhibitors of the HIV Protease," *Chem. Biol. 2001*, vol. 8, pp. 1161-1166. (Spec, p. 2).
Huckstep, M. and Richard J. K. Taylor, "A Convenient Method of Preparing the Leukotriene Precursor Methyl t-Oxopentanoate," *Communications*, 1982, pp. 881-882 (Spec, p. 9).

(Continued)

*Primary Examiner*—Brian-Yong S Kwon
*Assistant Examiner*—Bong-Sook Baek
(74) *Attorney, Agent, or Firm*—Collard & Roe, P.C.

(57) ABSTRACT

New peptidomimetic inhibitors of retroviral proteases are in particular for human immunodeficiency virus (HIV) protease. These inhibitors include as the core structure a new diamiriodiol isostere of the dipeptide Phe-Pro having four stereogenic centers. The inhibitors have been shown to inhibit HIV-protease and can therefore be usefully employed as antivirals for post-exposure prophylaxis and as a therapy for viral infections by a retrovirus, in particular HIV. The syntheses processes of the isosteres and inhibitors are also described.

2 Claims, 2 Drawing Sheets

OTHER PUBLICATIONS

Horner, L. et al., "Phosphororganische Verbindungen, XII: Phosphinoxyde als Olefinierungsreagenzien" (Organophosphorus Compounds, XII: Phosphinoxides as Reagents for Olefinations) *J. Chem. Soc.*, 1924, vol. 125, pp. 61-63. (With English Abstract) (Spec, pp. 9 and 11).

Wadsworth, Jr. William S., "The Utility of Phosphonate Cabanions in Olefin Synthesis," vol. 83, 1961, pp. 1733-1738. (Spec, pp. 9 and 11).

Ninomiya, K. et al., "Phosphorus in Organic Synthesis -VII," *Tetrahedron 1974*, vol. 30, pp. 2151-2157. (Spec, p. 10).

Giovannini, A. et al., "Organometallic Ring-Opening Reactions of N-Acyl and N-Alkoxycarbonyl Lactams..." *J. Org. Chem 1988*, vol. 54, pp. 228-234. (Spec, p. 11).

Lee, B-H. et al., "Selective Reduction of Secondary Amides to Amines in the Presence of Tertiary Amides," *Tetrahedron Letters 40*, 1999, pp. 643-644. (Spec, p. 11).

Takeuchi, Y. et al., "Synthesis and Antimarlarial Activity of *DL*-Deoxyfebrifugine," *Heterocycles 1999*, vol. 51, No. 8, pp. 1869-1875. (Spec, p. 11).

Benedetti, F. et al., "Facile Inversion of Configuration of N-Boc-β-aminoalcohols via $S_N2$ cyclization to oxazolidinones," *Tetrahedron Letters 41*, 2000, pp. 10071-10074. (Spec, p. 12).

Bonini C. et al., "An Easy Procedure for the Highly Regioselective Conversion of Epoxides to Halohydrins," *Synth Commun. 1992*, vol. 22, pp. 1863-1870. (Spec, p. 13).

Bonini C. and Giuliana Righi, "Regio- and Chemoselective Synthesis of Halohydrins by Cleavage of Oxiranes with Metal Halides," *Synthesis 1994*, pp. 225-238. (Spec, p. 13).

Koskinen, A. M., et al., "Synthetic Studies Towards Amino Alcohols . . . " *Tetrahedron Letters*, 1993, vol. 34, No. 42, pp. 6765-6758. (Spec, p. 13).

Frérot, E. et al., "PyBOP®[1] and PyBroP: Two Reagents for the Difficult Coupling of the α, α-Dialkyl Amino Acid, Aib" *Tetrahedron 1991*, vol. 47, pp. 259-270. (Spec, p. 15).

Carpino, Louis A., "1-Hydroxy-7-azabenzotriazole: An Efficient Peptide Coupling Additive," *J. Am. Chem. Soc. 1993*, vol. 115, pp. 4397-4398. (Spec, p. 15).

König, W. and Rolf Geiger, "A New Method for Synthesis of Peptides . . . " *Chem Ber. 1970*, vol. 103, pp. 788-798. (With English Abstract) (Spec, p. 15).

Toth, M. et al., "A simple, continuous flurometric assay for HIV protease," *Int. J. Peptide Protein Res.* 1990, vol. 36, pp. 544-550. (Spec, p. 16).

\* cited by examiner ced amide
PEPTIDOMIMETIC INHIBITORS OF RETROVIRAL PROTEASES AND THEIR USE AS ANTIVIRALS

CROSS REFERENCE TO RELATED APPLICATIONS

Applicants claim priority under 35 U.S.C. §119 of Italian Application No. PD2004A000151 filed Jun. 15, 2004. Applicants also claim priority under 35 U.S.C. §365 of PCT/EP2005/052770 filed Jun. 15, 2005. The international application under PCT article 21(2) was published in English.

FIELD OF THE INVENTION

The invention relates to new peptidomimetic inhibitors of retroviral proteases, and in particular human immunodeficiency virus (HIV) protease, bearing as the core structure diaminodiol isosteres of the dipeptide Phe-Pro, to their therapeutic use as antivirals for post-exposure prophylaxis and as a therapy for viral infections by a retrovirus, in particular HIV, and relative pharmaceutical compositions.

STATE OF THE ART

Generally, an effective anti-infective therapy has to eradicate the pathogenic agent or inhibit its proliferation without interfering with the physiological mechanisms of the host organism. In the case of retroviruses and in particular HIV the pathogenic agent responsible for acquired immunodeficiency syndrome (AIDS), research on substances able to selectively inhibit the replication cycle without damaging the host cell is rendered particularly difficult by the fact that the genome of the virus is integrated in that of the host, also exploiting its synthesis and enzyme systems. Expression of the integrated viral genome gives rise to RNA strands which control the synthesis of inactive polyproteins; these are subsequently partially hydrolysed to effect the complete maturation of new infected particles. Proteolysis by a protease of the host cell supplies the structural proteins of the virus, while the enzymes necessary for its replication are generated by a retroviral protease. All the retroviral proteases up to now described belong to the class of aspartic proteases and are active as symmetrical homodimers containing a single active site. This type of architecture is unique among proteolytic enzymes. The catalytic activity of retroviral proteases is due to two aspartic acid residues (Asp25 and Asp25' in HIV protease), present inside the active site, which, by means of a general type acid-base catalysis, activate the nucleophilic attack of a water molecule on the scissile amide bond of the natural polyprotein. HIV protease (hereinafter also indicated by HIV-PR) is an enzyme essential to the replication cycle of the virus: hydrolysing the polyproteins $PR55^{gag}$ and $PR160^{gag/pol}$ enables the formation of new infected particles. It has indeed been demonstrated that virions containing catalytically inactive proteases cannot achieve maturation (Kohl, N. et al. *Proc. Natl. Acad. Sci. USA* 1988, 85, 4686). The crucial role performed by this enzyme in the replication cycle makes it one of the better targets for anti-HIV therapy and one of the most studied and well-known in terms of structure and function (Kramer, R. A. et al. *Science* 1986, 231, 1580; Huff, J. R. *J. Med. Chem.* 1991, 34, 2305). HIV protease is able to hydrolyse various types of amide bonds, including those with proline as N-terminal residue (specifically the amide bonds Tyr-Pro or Phe-Pro). Hydrolysis of proline amide bonds is somewhat rare, being a peculiarity of retroviral proteases (Griffiths, J. T. et al. *J. Biochemistry* 1992, 31, 5193); in mammals in particular, cellular proteases having the same specificity are unknown (Kräusslich, H.-G. et al. *Proc. Natl Acad. Sci. USA* 1989, 86, 807; Graves, M. C. et al. *Biochem. Biophys. Res. Commun.* 1990, 168; 30). The introduction of HIV protease inhibitors, in the second half of the 1990's, represented a mile stone in the development of an effective anti-AIDS therapy. Most of the inhibitors which have so far been developed are "peptidomimetic" of general structure $P_n \ldots P_2-(P_1-[\phi]-P_1')-P_2' \ldots P_n'$, which bind reversibly to the enzyme by means of non-covalent interactions. The central portion of these inhibitors $(P_1-[\phi]-P_1')$ is represented by the isostere of a dipeptide, defined as a stable functional group able to reproduce the stereoelectronic characteristics of a dipeptide but which cannot be hydrolysed by protease. The following structures have been frequently used as isosteres in the synthesis of HIV-protease inhibitors: diamino alcohol —HN—CH($P_1$)—CH(OH)—CH$_2$—CH($P_1'$)—NH—; diamino diol —HN—CH($P_1$)—CH(OH)—CH(OH)—CH($P_1'$)—NH—; phosphoramide —HN—CH($P_1$)—PO$_2$—NH—CH($P_1'$)—CO—, reduced amide —HN—CH($P_1$)—CH$_2$—NH—CH($P_1'$)—CO—, fluoroketone —HN—CH($P_1$)—CO—CF$_2$—CH($P_1'$)—CO—, statine —HN—CH($P_1$)—CH(OH)—CH$_2$—CO—, norstatine —HN—CH($P_1$)—CH(OH)—CO—NH—, ketoamide —HN—CH($P_1$)—CO—CO—NH—, hydroxyethyl amine —HN—CH($P_1$)—CH(OH)—CH$_2$—NH—, dihydroxyethylene —HN—CH($P_1$)—CH(OH)—CH(OH)—CH($P_1'$)—CO—, hydroxyethylene —HN—CH($P_1$)—CH(OH)—CH$_2$—CH($P_1'$)—CO—. (Wlodawer, A., Erickson, J. W. *Ann. Rev. Biochem.* 1993, 62, 543; Martin, J. A. et al. *Progr. in Med. Chem.* 1995, 32, 239; Chen, C. A. et al. *Chem. Biol.* 2001, 8, 1161).

Seven HIV-protease inhibitors have been approved by the FDA as anti-AIDS therapy drugs: Amprenavir [Agenerase®; Glaxo-SmithKline; (3S)-tetrahydro-3-furyl N-[(1S,2R)-3-(4-amino-N-isobutyl-benzenesulfonamide)-1-benzyl-2-hydroxypropyl] carbamate]; Atazanavir [Reyataz®; Bristol-Meyers Squibb; sulfate (1:1) of the dimethyl ester of (3S,8S,9S,12S)-3,12-bis(1,1-dimethylethy)-8-hydroxy-4,11-dioxo-9-(phenylmethyl)-6-[[4-(2-piridinyl)phenyl]methyl]-2,5,6,10,13-pentaazatetradecandioic] acid; Indinavir [Crixivan®; Merck; [1(1S,2R),5(S)]-2,3,5-trideoxy-N-(2,3-dihydro-2-hydroxy-1H-inden-1-yl)-5-[2-[[(1,1-dimethylethyl)amino]carbonyl]-4-(3-piridinylmethyl)-1-piperazinyl]-2-(phenylmethyl)-D-erythro-pentanamide sulfate (1:1)]; Lopinavir [Kaletra® (Lopinavir and Ritonavir combination; Abbott Laboratories)]; [1S-[1R,(R*),3R*,4R*]]-N-[4-[[2,6-dimethylphenoxyacetyl]amino]-3-hydroxy-5-phenyl-1-(phenylmethyl)pentyl]tetrahydro-alpha-(1-methylethyl)-2-oxo-1 (2H)-pyrimidinacetamide]; Nelfinavir [Viracept®; Agouron Pharmaceuticals and Pfizer; [3S-[2(2S*,3S*), 3 alpha,4a beta,8a beta]]-N-(1,1-dimethylethyl) decahydro-2-[2-hydroxy-3-[(3-hydroxy-2-methylbenzoyl)amino]-4-(phenylthio)butyl]-3-isoquinolinecarboxamide mono-methanesulfonate]; Ritonavir [Norvir®; Abbott Laboratories; [5S-(5R*,8R*,10R*,11R*)] 10-hydroxy-2-methyl-5-(1-methylethyl)-1-[2-(1-methylethyl)-4-thiazolyl]-3,6-dioxo-8,11-bis(phenylmethyl)-2,4,7,12-tetraazadecan-13-oic acid 5-thiazolylmethyl ester] and Saquinavir [Fortovase®; Roche; N-tert-butyl-decahydro-2-[2(R)-hydroxy-4-phenyl-3(S)-[[N-(2-quinolylcarbonyl)-L-asparaginyl]amino]butyl]-(4aS,8aS)-isoquinoline-3(S)-carboxamide; Invirase®; Roche; methanesulfonate of N-tert-butyl-decahydro-2-[2(R)-hydroxy-4-phenyl-3(S)-[[N-(2-quinolylcarbonyl)-L-asparaginyl]amino]butyl]-(4aS,8aS)-isoquinoline-3(S)-carboxamide]. These are all peptidomimetics based on phenylalanine isosteres containing hydroxyl groups.

By reducing the number of very evident AIDS cases and the mortality associated therewith, antiretroviral therapy represents a considerable success in the treatment of HIV infection. However the protease inhibitors used in the antiretroviral therapy present some disadvantages and some side effects, namely: i) toxicity; ii) reduced solubility with resultant poor bioavailability of the active principle and the consequent need to repeatedly consume the drugs over the course of a day; iii) onset of lipid and carbohydrate metabolism disorders due to the inhibitors interfering with cellular aspartic proteases; iv) development of viral strains resistant to the drugs, and to combinations thereof, due to transcription errors during DNA replication and associated with an increased virus replication rate. The pandemic nature of the disease and the limitations of therapeutic regimens therefore necessitate the development of new and more effective therapies.

SUMMARY OF THE INVENTION

For the purpose of identifying new compounds able to inhibit retroviral proteases and in particular HIV-PR, the inventors have identified a new isostere of the dipeptide phenylalanine-proline (Phe-Pro) on which said compounds are based. The invention therefore provides retroviral protease inhibitors of general formula (I)

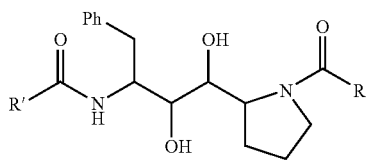

(I)

and their pharmaceutically acceptable salts or esters in which R and R' can be independently one from the other residues of amino acids, peptides and carboxylic acids, and the diaminodiol isostere of the dipeptide phenylalanine-proline of formula (II)

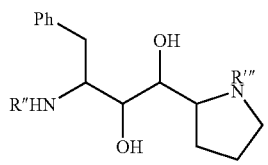

(II)

in which R" and R'" can be independently one from the other equal to hydrogen or groups protecting the terminal amino group.

The invention also provides the use of the inhibitors of the invention for the post exposure prophylaxis and/or antiviral therapy of infections from retroviral agents, the compositions containing them, and the processes for their synthesis.

DETAILED DESCRIPTION OF THE INVENTION

Figure 1:
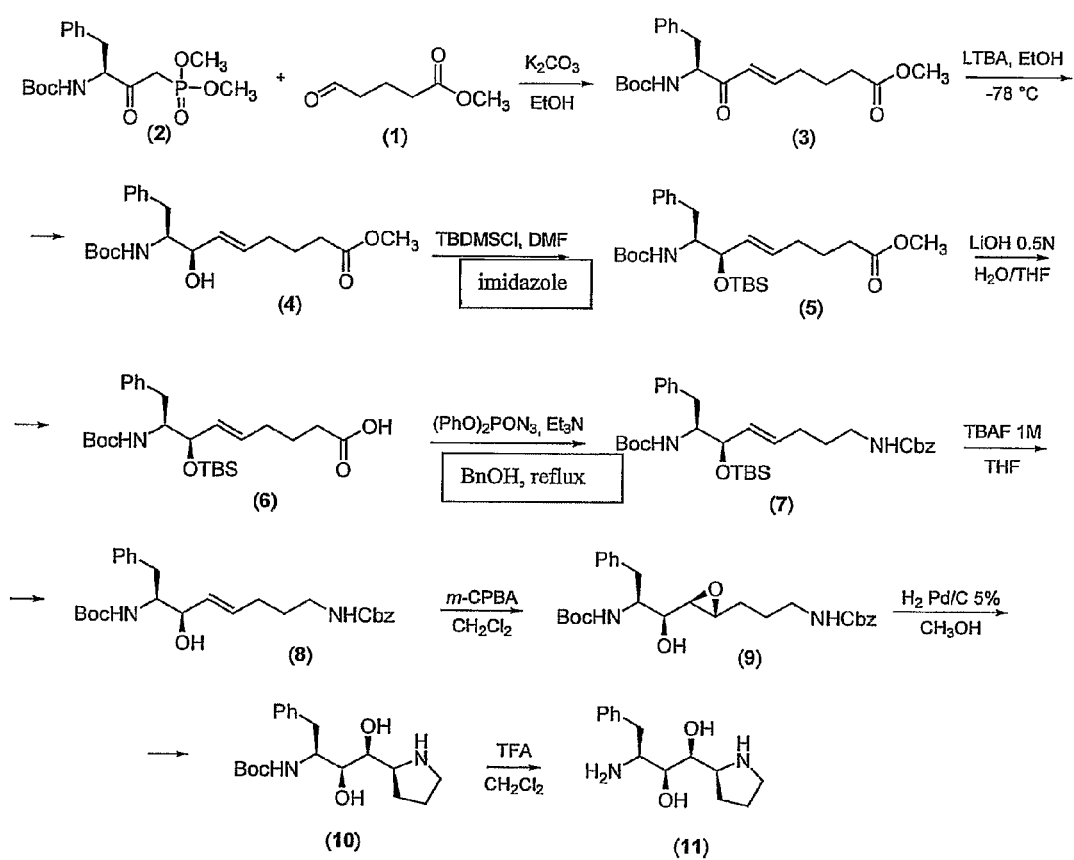
FIG. 1: synthesis scheme of the Phe-Pro isostere (1S,2S,3S)-3-amino-4-phenyl-1-[(2S)-pyrrolidin-2-yl]butan-1,2-diol.

The purposes and advantages of the retroviral protease inhibitors of the invention and their therapeutic use as antivirals in infections from retroviral agents, in particular HIV, will be better understood in the course of the following detailed description which, by way of non-limiting examples of the invention, describes the synthesis of the Phe-Pro dipeptide isostere of formula (II) in its four different stereochemical configurations, the synthesis of the inhibitors which comprise them and, by way of example, the ability of the synthesised inhibitors to inhibit HIV-PR in vitro.

The retroviral protease inhibitors of general formula (I) of the invention

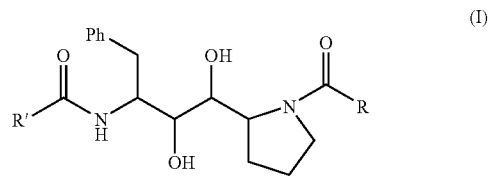

(I)

and their pharmaceutically acceptable salts or esters in which R and R' can be independently one from the other amino acid residues, peptides, carboxylic acids and combinations thereof, comprise as basic structure the new diaminodiol-type Phe-Pro isostere of formula (II) previously shown.

The isostere of formula (II) in which R" and R'" have independently one from the other the aforegiven meanings of hydrogen or groups protective of the terminal amino group, can be synthesised in accordance with a stereoselective method devised by the inventors, the four stereogenic centres assuming four different configurations: S,S,S,S or S,R,R,S or S,R,R,R or S,S,R,R and, when R" and R'" are groups protective of the terminal amino group, these are preferably chosen from the group comprising carbamates (in particular tert-butyl (Boc) and benzyl carbamate (Cbz).)

As a consequence the retroviral protease inhibitors of the invention can also have one of the four stereochemical configurations mentioned and can therefore have the formula (III)

the formula (III)

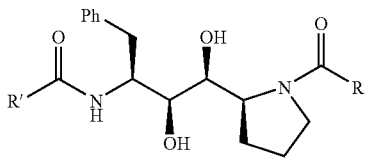

(III)

of formula (IV)

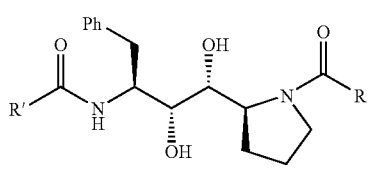

(IV)

of formula (V)

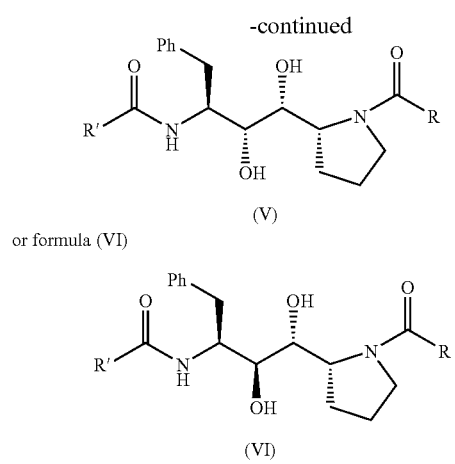

(V)

or formula (VI)

(VI)

in which R and R' have the aforegiven meaning.

Regarding in particular the inhibitors of the invention, the R and R' residues, being the same or different, can be preferably chosen from the groups comprising:

a) α-amino acids of the L or D series, optionally also substituted;

b) peptide chains of general structure Xaa-Yaa-Zaa consisting of two or three residues of said α-amino acids of the L and D series;

c) carboxylic acids containing up to twelve carbon atoms, having at least one aromatic or heteroaromatic group in which the aromatic ring can be optionally substituted by alkyl groups.

More preferably, but non-limitingly, when R and R' are residues of α-amino acids of the L or D series, optionally also substituted, these can be chosen from the group comprising Valine, Leucine, Isoleucine, Serine, Threonine, Tryptophan, Glutamic Acid, Glycine, Thienylglycine, Phenylalanine and Cyclohexilalanine. When R, R' are peptide chain residues of general structure Xaa-Yaa-Zaa consisting of two or three amino acids, these can more preferably be: Xaa: Valine, Leucine, Isoleucine, Thienylglycine, Asparagine; Yaa: Valine, Leucine, Tryptophan, Phenylalanine and Cyclohexilalanine; Zaa: Serine, Threonine. When R, R' are carboxylic acids containing up to twelve carbon atoms, having at least one aromatic or heteroaromatic group optionally substituted by alkyl groups, these are preferably, but non-limitingly, derivatives of phenoxyacetic acid and kynurenic acid substituted with methyl groups.

Using the new Phenylalanine-Proline isostere of formula (II) for the retroviral proteases inhibitors of the invention can be particularly advantageous in that the pyrrolidine residue enables a structure analogous to that of the natural substrate to be present at the scissile bond; this structure can therefore be recognised with high affinity inside the catalytic site, whereas the hydrolytic activity of the protease can be inhibited by the presence of the central diol.

Regarding the synthetic approach, the inventors have previously devised a general methodology for the stereoselective synthesis of diaminodiols of general structure H$_2$N—CH(R$_1$)—CH(OH)—CH(OH)—CH(R$_2$)—NH$_2$ and S configuration at each of the four stereogenic centres (Benedetti, F. et. al. *J. Org. Chem.* 1997, 62, 9348), based on the regio- and stereoselective reaction of ammonia or azide with N-Boc protected epoxyalcohols (BocNH—CH(R$_1$)—CH(OH)—CH(O)CH(R$_2$)) derived from the α-amino acids BocNH—CH(R$_1$)—COOH. In this synthesis the two terminal amino groups of the diaminodiols H$_2$N—CH(R$_1$)—CH(OH)—CH(OH)—CH(R$_2$)—NH$_2$ can be differentiated by means of orthogonal protective groups, the approach described being applicable to the synthesis of diaminodiols with not necessarily identical R$_1$ and R$_2$ residues.

This approach, however, cannot be applied to the synthesis of dipeptide isosteres of general structure Xaa-Pro which require the presence of a cyclic system analogous or similar to that present in the natural amino acid proline. The new synthetic process is based on the intramolecular opening of an epoxide ring by an amino group suitably positioned at the end of the chain of an intermediate tert-butyl 1-[3-(3-aminopropyl)oxiran-2-yl]-1-hydroxy-3-phenylpropan-2-ylcarbamate thus generating the desired pentatomic ring as shown below:

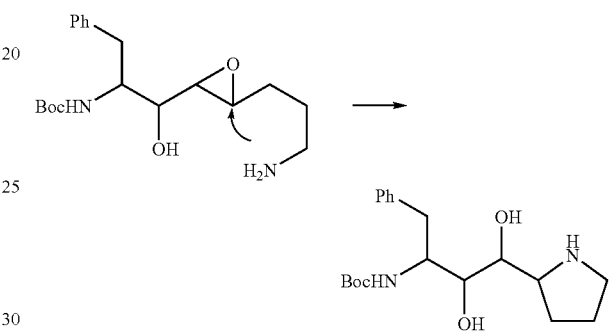

In particular, the new methodology devised by the inventors provides the new Phe-Pro isostere to be obtained in the required stereoisomeric form through the following steps:

synthesis of an aldehyde starting from a suitable lactone;

synthesis of a dimethyl-β-ketophosphonate starting from a suitable α aminoacid;

olefination under Horner-Emmons conditions;

reduction of the enone obtained in the previous step to obtain the corresponding allylic alcohol;

configuration inversion through formation and subsequent hydrolysis of an oxazolidinone;

protection of the hydroxy group of the allylic alcohols obtained;

hydrolisis of a terminal methyl ester group;

insertion of a second aminic group through "Curtius rearrangement" reaction deprotection of the hydroxy group;

epoxidation of an amino-alcohol;

removal of a protecting group by catalytic hydrogenation and subsequent intramolecular cyclization.

By this process the new Phe-Pro isostere is obtained in the required stereoisomeric form starting from δ-valerolactone and L-phenylalanine methyl ester, as given in the scheme in FIG. 1 and described hereinafter.

In the first step, the aldehyde methyl 5-oxo-pentanoate (1) is obtained from δ-valerolactone in two passages as described by Huckstep (Huckstep, M.; Taylor, R. J. K.; Canton, M. P. L. *Synthesis* 1982, 881).

In parallel, N-Boc-L-phenylalanine methyl ester is converted into the corresponding dimethyl-β-ketophosphonate (dimethyl (3S)-3-[(tert-butoxycarbonyl)amino]-2-oxo-4-phenylbutyl-phosphonate) (2) by treating with dimethyl-methylphosphonate and n-butyllithium (Benedetti, F. et. al. *J. Org. Chem.* 1997, 62, 9348). The olefination with methyl 5-oxo-pentanoate (1) under Horner-Emmons conditions (Horner, L. et al. *Chem. Ber.* 1958, 91, 61; Wadsworth, Jr., W. S.; Emmons, W. D. *J. Am. Chem. Soc.* 1961, 83, 1733) of the previously obtained N-Boc-phosphonate (2) provides methyl (5E,8S)-8-[(tert-butoxycarbonyl)amino]-7-oxo-9-phenyl-non-5-enoate (3) as the only product; the stereochemistry trans of the double bond is confirmed by a NMR spectrum (coupling constant between the two vinylic protons equal to 15.6 Hz).

The next step is the reduction of the α,β,-unsaturated carbonyl with lithium tri-tert-butoxyaluminium hydride (LTBA) in ethanol to give the corresponding allylic alcohol (methyl (5E,7R,8S)-8-[(tert-butoxycarbonyl)amino]-7-hydroxy-9-phenyl-non-5-enoate) (4). At this point the allylic hydroxy group is temporarily protected as tent-butyl-dimethylsilyl ether to give methyl (5E,7R,8S)-8-[(tert-butoxycarbonyl)amino]-7-[(tert-butyl-dimethyl-silanyl)oxy]-9-phenyl-non-5-enoate (5) and then the terminal ester group is hydrolysed, thus obtaining free carboxylic acid (5E,7R,8S)-8-[(tert-butoxycarbonyl)amino]-7-[(tert-butyl-dimethyl-silanyl)oxy]-9-phenyl-non-5-enoic acid) (6). The second amino group is introduced at this point of the synthesis by treating the acid with diphenyl phosphoryl azide, triethylamine and benzyl alcohol (Ninomiya, K. et al. *Tetrahedron* 1974, 30, 2151) which gives benzyl (4E,6R,7S)-7-[(tert-butoxycarbonyl)amino]-6-[(tert-butyl-dimethyl-silanyl)oxy]-8-phenyl-oct-4-enylcarbamate (7), having one atom of carbon less than the starting acid, and an amino group in the ω position orthogonally protected as Cbz. The next step is the deprotection of the allylic hydroxy group with tetrabutylammonium fluoride (TBAF) to give benzyl (4E,6R,7S)-7-[(tert-butoxycarbonyl)amino]-6-hydroxy-8-phenyl-oct-4-enylcarbamate (8). The epoxidation of the double bond of this allylic alcohol with m-chloroperbenzoic acid is controlled by the free hydroxy group and gives, as the main product, benzyl 3-((2R,3R)-3-{[(1S,2S)-1-hydroxy-2-[(tert-butoxycarbonyl)amino]-3-phenylpropyl}oxiran-2-yl)propylcarbamate (9).

The following step is the removal of the protecting group Cbz by catalytic hydrogenation which frees the amino group; the tert-butyl (1S,2S)-1-[(2R,3R)-3-(3-aminopropyl)oxiran-2yl]-1-hydroxy-3-phenylpropan-2-ylcarbamate thus obtained cyclizes spontaneously to give tert-butyl (1S,2S, 3S)-1-benzyl-2,3-dihydroxy-3-[(2S)-pyrrolidin-2-yl]propyl-carbamate (10). Finally, by deprotecting this latter compound with trifluoroacetic acid (TFA), the (1S,2S,3S)-3-amino-4-phenyl-1-[(2S)-pyrrolidin-2-yl]butan-1,2-diol (11) isostere of the new diaminodiol Phe-Pro isostere of formula (II) is obtained.

This methodology consists of 11 steps with a 20% average recover. The possibility of decreasing the number of synthetic steps and, at the same time, improving the final yield has led to the development of alternative conditions and to the optimization of the process.

This second process provides the new Phe-Pro isostere to be obtained in the required stereoisomeric form through the following steps:
synthesis of a suitable protected lactam;
synthesis of a dimethyl-β-ketophosphonate starting from a suitable a aminoacid;
olefination under Horner-Emmons conditions;
stereoselective reduction of the enone obtained in the previous step to obtain the corresponding allylic alcohol;
epoxidation of an amino-alcohol;
removal of a protecting group by catalytic hydrogenation and subsequent intramolecular cyclization.

In particular, 2-pyrrolidinone is N-benzoylated using benzyl chloroformate and n-butyllithium (Giovannini, A. et al *J. Org Chem.* 1989, 54, 228) and then reduced to N-Cbz-pyrrolidinol using lithium borohydride (Lee, B. H. et al *Tetrahedron Lett.* 1999, 40, 643). In the meantime, the reaction of N-Boc-L-phenylalanine methyl ester with dimethyl-methylphosphonate and n-buthyllithium affords the corresponding dimethyl-β-ketophosphonate ((3S)-3-[(tert-butoxycarbonylamino]-2-oxo-4-phenyl-butyl)-phosphonic acid dimethyl ester) (2) (Benedetti, F. et. al. *J. Org. Chem.* 1997, 62, 9348). Olefination of the N-Boc-ketophosphonate (2) with the reduced lactam under Horner-Emmons conditions (Horner, L. et al. *Chem. Ber.* 1958, 91, 61; Wadsworth, Jr., W. S.; Emmons, W. D. *J. Am. Chem. Soc.* 1961, 83, 1733; Takeuchi, Y. et al *Heterocycles* 1999, 51, 1869) gives (4E,7S)-7-[(tert-butoxycarbonylamino]-6-oxo-8-phenyl-oct-4-enyl)-carbamic acid benzyl ester as the only product, whose E configuration is assigned on the base of the coupling constant (J=15.6 Hz) of the olefinic protons seen in the $^1$H-NMR. The following step is the stereoselective reduction of the α,β-unsaturated enone with tri-tert-butoxy lithium aluminium hydride (LTBA), in ethanol, affording the allylic alcohol (4E, 6R,7S)-7-[(tert-butoxycarbonylamino]-6-hydroxy-8-phenyl-oct-4-enyl)carbamic acid benzyl ester (8). The epoxidation of the allylic alcohol double bond with m-chloroperbenzoic acid, the removal of the Cbz protecting group by catalytic hydrogenation, the spontaneous intramolecular cyclization, as already described for the other possible approach, give the isostere (1S,2S,3S)-1-benzyl-2,3-dihydroxy-3-[(2S)-pyrrolidin-2-yl]propyl-carbamic acid tert-butyl ester (10), that can be deprotected with trifluoroacetic acid (TFA) finally affording the (1S,2S,3S)-3-amino-4-phenyl-1-[(2S)-pyrrolidin-2-yl]butane-1,2-diol (11) isostere of the new diaminodiolic Phe-Pro isostere (II).

Using a similar approach, by way of an initial configuration inversion at the C-7 of methyl (5E,7R,8S)-8-[(tert-butoxycarbonyl)amino]-7-hydroxy-9-phenyl-non-5-enoate (4) the isomers [(1S,2R,3R)-3-amino-4-phenyl-1-[(2S)-pyrrolidin-2-yl]butan-1,2-diol] (12) and [(1S,2R,3R)-3-amino-4-phenyl-1-[(2R)-pyrrolidin-2-yl]butan-1,2-diol] (13) of the new diaminodiol Phe-Pro isostere of formula (II) can be obtained

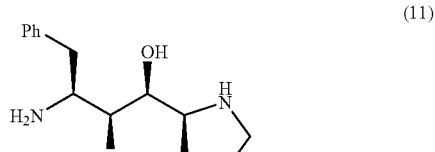

(11)

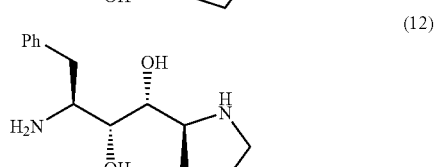

(12)

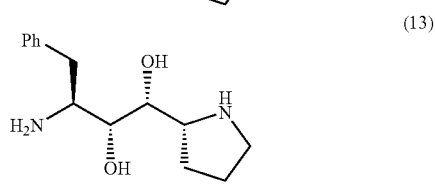

(13)

Figure 2:
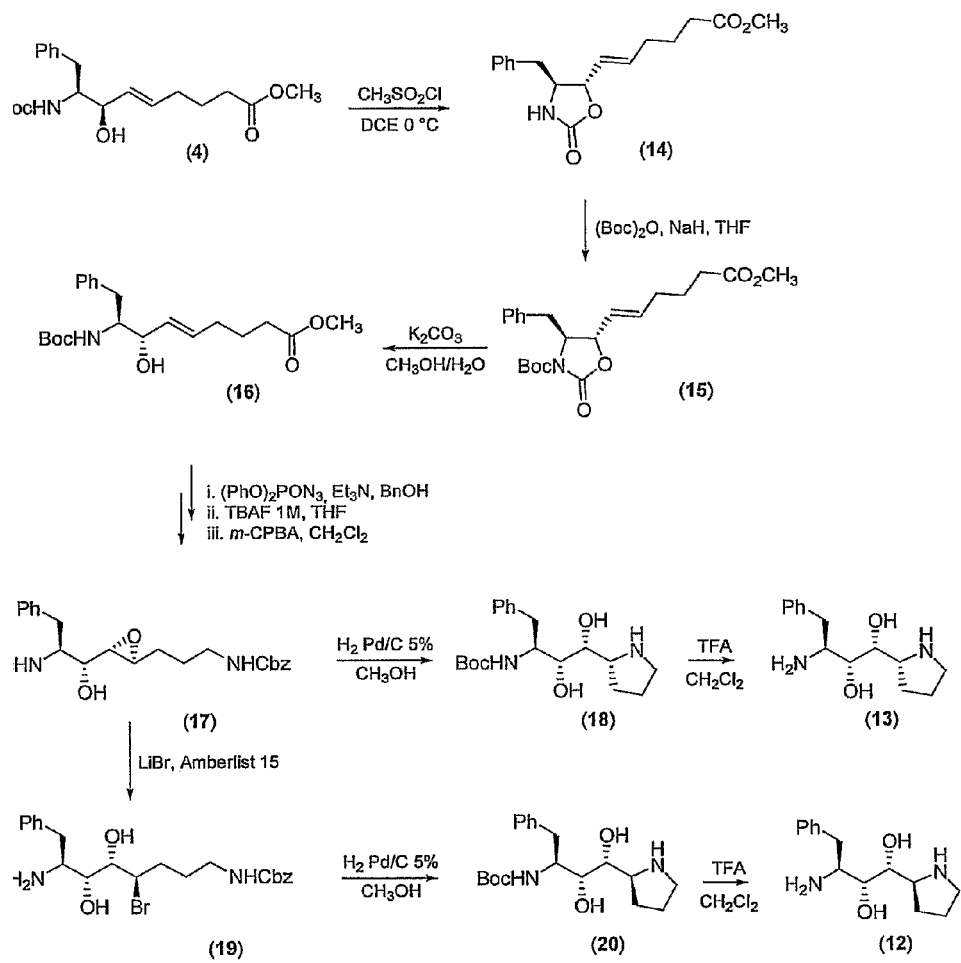
FIG. 2: synthesis scheme of the Phe-Pro (1S,2R,3R)-3-amino-4-phenyl-1-[(2S)-pyrrolidin-2-yl]butan-1,2-diol and (1S,2R,3R)-3-amino-4-phenyl-1-[(2R)-pyrrolidin-2-yl]butan-1,2-diol isosteres.

The synthesis scheme of the isomers (12) and (13) is described below and is shown in FIG. 2.

The configuration inversion at C-7 of the methyl (5E,7R, 8S)-8-[(tert-butoxycarbonyl)amino]-7-hydroxy-9-phenyl-non-5-enoate (4) is obtained in three steps. Initially the amino alcohol (4) is converted to oxazolidinone by treating with methanesulfonyl chloride (Benedetti, F.; Norbedo, S. *Tetrahedron Lett.* 2000, 39, 10071); thus methyl (5E)-6-[(4S,5S)-4-benzyl-2-oxo-1,3-oxazolidin-5-yl]hex-5-enoate (14) is obtained. The oxazolidinone is reprotected at the nitrogen with di-tert-butyl dicarbonate to give (4S,5S)-tert-butyl 5-[(E)-5-(methoxycarbonyl)pent-1-enyl]-4-benzyl-2-oxooxazolidin-3-carboxylate (15) which is then hydrolysed under controlled conditions (two equivalents of $K_2CO_3$, or $Cs_2CO_3$) in aqueous methanol. The methyl (5E,7S,8S)-8-[(tert-butoxycarbonyl)amino]-7-hydroxy-9-phenyl-non-5-enoate (16) with (S) configuration at the C7 thus obtained is then converted, by applying the aforedescribed method for the synthesis of benzyl 3-((2R,3R)-3-{[(1S,2S)-1-hydroxy-2-[(tert-butoxycarbonyl)amino]-3-phenylpropyl}oxiran-2-yl)propylcarbamate (9), to benzyl 3-((2S,3S)-3-{[(1R,2S)-1-hydoxy-2-[(tert-butoxycarbonyl)amino]-3-phenylpropyl}oxiran-2-yl)propylcarbamate (17). By deprotecting this epoxyamine by catalytic hydrogenation, tert-butyl (1S,2R,3R)-1-benzyl-2,3-dihydroxy-3-[(2R)-pyrrolidin-2-yl]propylcarbamate (18) is thus obtained which is converted into the corresponding [(1S,2R,3R)-3-amino-4-phenyl-1-[(2R)-pyrrolidin-2-yl]butan-1,2-diol] (13) by treating with TFA. Opening the epoxide ring of benzyl 3-((2S,3S)-3-{[(1R,2S)-1-hydoxy-2-[(tert-butoxycarbonyl)amino]-3-phenylpropyl}oxiran-2-yl)propylcarbamate (17) with lithium bromide and Amberlist 15 (Bonini, C. et al. *Synth. Commun.* 1992, 22, 1863; Bonini, C., Righi, G. *Synthesis* 1994, 225) gives the bromoalcohol benzyl (4R,5R,6R,7S)-4-bromo-7-[(tert-butoxycarbonyl)amino]-5,6-dihydroxy-8-phenyl-octylcarbamate (19) which, by catalytic hydrogenation, cyclizes to give tert-butyl (1S,2R,3R)-1-benzyl-2,3-dihydroxy-3-[(2S)-pyrrolidin-2-yl]propylcarbamate (20); finally, deprotecting the primary amino group with TFA gives [(1S,2R,3R)-3-amino-4-phenyl-1-[(2S)-pyrrolidin-2-yl]butan-1,2-diol] (12).

Alternatively, through a first inversion of the configuration at the C-6 in (4E,6R,7S)-7-[(tert-butoxycarbonylamino]-6-hydroxy-8-phenyl-oct-4-enyl)carbamic acid benzyl ester (8) and using a similar approach, it's possible to obtain the two isomers [(1S,2R,3R)-3-amino-4-phenyl-1-[(2S)-pyrrolidin-2-yl]butane-1,2-diol] (12) and [(1S,2R,3R)-3-amino-4-phenyl-1-[(2R)-pyrrolidin-2-yl]butane-1,2-diol] (13) of the new diaminodiolic isostere Phe-Pro (II).

The inversion of the configuration at the C-6 in (4E,6R,7S)-7-[(tert-butoxycarbonylamino]-6-hydroxy-8-phenyl-oct-4-enyl)carbamic acid benzyl ester (8) can be easily obtained reducing the enone, rising from the reaction between N-Boc-ketophosphonate (2) and the N-Cbz pyrrolidinol, with L-Selectride (Koskinen, A. M. *Tetrahedron Lett.* 1993, 34, 42, 6765), affording (4E,6R,7S)-7-[(tert-butoxycarbonylamino]-6-hydroxy-8-phenyl-oct-4-enyl)carbamic acid benzyl ester. Proceeding as above, the isosteres (12) and (13), eventually in their protected form, are easily and quickly synthesized.

Eventually, using the benzyl 3-((2S,3S)-3-{[(1S,2S)-1-hydroxy-2-[(tert-butoxycarbonyl)amino]-3-phenylpropyl}oxiran-2-yl)propylcarbamate, recoverable as a by-product from the epoxidation with m-chloroperbenzoic acid of the allylic alcohol (4E,6R,7S)-7-[(tert-butoxycarbonyl)amino]-6-hydroxy-8-phenyl-oct-4-enylcarbamate (8), and following an approach similar to the one already described for the synthesis of tert-butyl (1S,2S,3S)-1-benzyl-2,3-dihydroxy-3-[(2S)-pyrrolidin-2-yl]propylcarbamate (10), tert-butyl (1S,2S,3R)-1-benzyl-2,3-dihydroxy-3-[(2R)-pyrrolidin-2-yl]propylcarbamate can be obtained as a possible fourth diaminodiol (S,S,R,R) Phe-Pro isostere.

The retroviral protease inhibitors of the invention can be synthesized starting from these isosteres by conventional synthesis processes with coupling reactions between said isosteres of general formula (II) (hereinafter also identified as Phe[φ]Pro) and residues of amino acids, peptides and carboxylic acids.

For the purposes of non-limiting illustration of the present invention the (1S,2S,3S)-3-amino-4-phenyl-1-[(2S)-pyrrolidin-2-yl]butan-1,2-diol (11) isostere or its protected form (10), was used as core units for the synthesis of the peptidomimetic inhibitors of HIV protease (21), (22), (23), (24), (25):

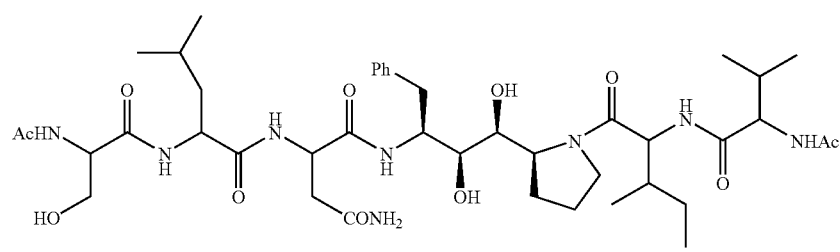

(21)

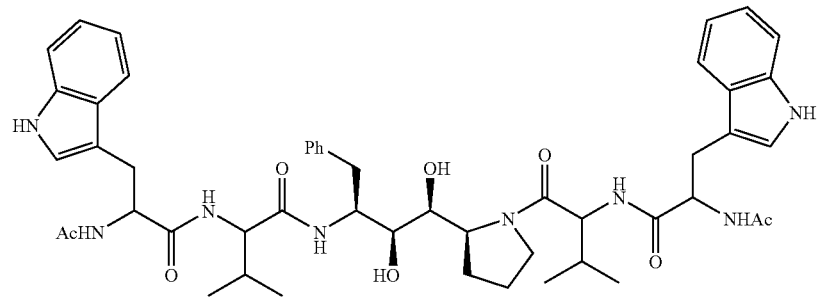

(22)

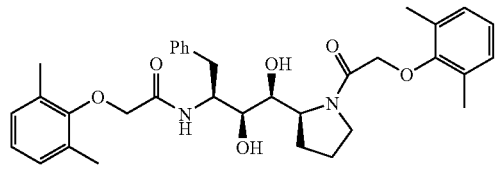
(23)

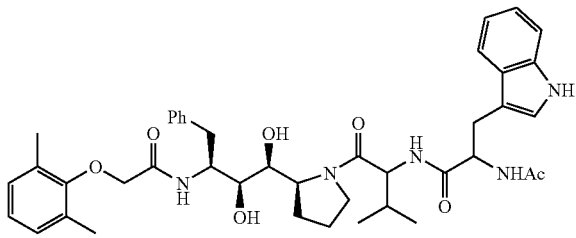
(24)

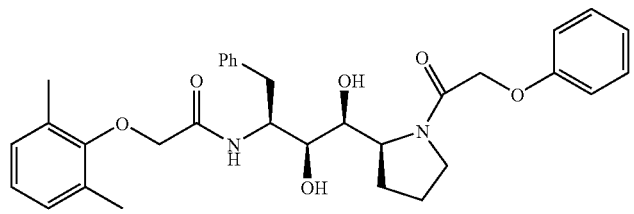
(25)

In the case of inhibitors (22) and (23), in which the R and R' groups are the same, the (1S,2S,3S)-3-amino-4-phenyl-1-[(2S)-pyrrolidin-2-yl]butan-1,2-diol (11) is reacted respectively with 2 equivalents of the acetylated dipeptide Ac-NH-Trp-Val-OH in the presence of benzotriazole-1-yl-oxy-trispyrrolidino-phosphonium hexafluorophosphate (PYBOP®) and 1H-hydroxybenzotriazole (HOBT) as activating agents (Frerot, E. et al. *Tetrahedron* 1991, 47, 259) and with 2 equivalents of 2,6-dimethyl-phenoxyacetic acid (DmPoa) in the presence of N-ethylcarbodiimide (EDC) and (HOBT) as activating agents (Carpino, L. A. *J. Am. Chem. Soc.* 1993, 115, 4397; Konig, W.; Geiger, R. *Chem. Ber.* 1970, 103, 788). The inhibitors (21), (24), (25) which contain different R and R' groups were instead synthesised starting from tert-butyl (1S,2S,3S)-1-benzyl-2,3-dihydroxy-3-[(2S)-pyrrolidin-2-yl]propylcarbamate (10) introducing the R and R' residues independently. For the synthesis of (21), (1S,2S,3S)-1-benzyl-2,3-dihydroxy-3-[(2S)-pyrrolidin-2-yl]propylcarbamate (10) was reacted, in the stated order, with the separately prepared acetylated dipeptide AcNH-Val-Ile-OH in the presence of PYBOP® and HOBT as activating agents, then with TFA for deprotecting from Boc and finally with the acetylated tripeptide AcNH-Ser-Leu-Asn-OH in the presence of PYBOP® and HOBT.

For the synthesis of (25) the same carbamate (10) was reacted, in the stated order, with phenoxyacetic acid (Poa) in the presence of EDC and HOBT as activating agents, then with TFA for deprotecting from Boc and finally with 2,6-dimethylphenoxyacetic acid (DmPoa) in the presence of EDC and HOBT.

The inhibitor (24) was obtained from the same carbamate (10) in five passages, as follows: the tert-butyl (1S,2S,3S)-1-benzyl-2,3-dihydroxy-3-[(2S)-pyrrolidin-2-yl]propylcarbamate (10) was reacted with N-Cbz-valine in the presence of PYBOP® and HOBT; with hydrogen in the presence of palladium on carbon for deprotecting the Cbz group; with N-Ac-tryptophan in the presence of PYBOP® and HOBT; with TFA for deprotecting the Boc group; with DmPoa in the presence of EDC and HOBT.

Without departing from the scope of the invention, analogous inhibitors can be synthesized starting from the others isomers of the new diaminodiol Phe-Pro isostere of formula (II).

The in vitro activity of the inhibitors (21), (22), (23), (24), (25) was evaluated in a standard assay conducted with HIV-protease and a fluorogenic substrate (Toth, M. et al. *Int. Peptide Protein Res.* 1990, 36, 544), given as the concentration corresponding to 50% inhibition ($IC_{50}$) in table 2.

EXPERIMENTAL PART

Example 1

Synthesis of the isostere (1S,2S,3S)-3-amino-4-phenyl-1-[(2S)-pyrrolidin-2-yl]butan-1,2-diol (11)

1.a) Preparation of methyl (5E,8S)-8-[(tert-butoxycarbonyl)amino]-7-oxo-9-phenyl-non-5-enoate (3)

A solution of aldehyde (methyl 5-oxopentanoate) (1) (3.0 g, 23.1 mmol), in absolute ethanol (100 mL) is added, under stirring, to a solution of dimethyl (3S)-3-[(tert-butoxycarbonyl)amino]-2-oxo-4-phenylbutyl-phosphonate (2) (8.58 g, 23.1 mmol) and $K_2CO_3$ (3.2 g, 23.1 mmol), dried at 75° C. for 12 hours, in absolute ethanol (200 mL). The mixture is then stirred at room temperature for 16 hours, the solid residue is filtered off and the solution neutralised with glacial acetic acid. The solvent is removed under reduced pressure and the residue partitioned between ethyl acetate and a saturated solution of $NaHCO_3$. The aqueous phase is extracted with ethyl acetate (2×50 mL) and the pooled organic phases are washed with a saturated NaCl solution and dried over anhydrous $Na_2SO_4$. The solvent is removed by distilling under reduced pressure and the product purified by means of flash chromatography on a silica gel column by using a 1:1 mixture of ethyl ether and petroleum ether as eluant. 6.8 g (79%) of a colourless oil are obtained.

1.b) Preparation of methyl (5E,7R,8S)-8-[(tert-butoxycarbonyl)amino]-7-hydroxy-9-phenyl-non-5-enoate (4)

Lithium tri-tert-butoxyaluminiumhydride (1.37 g, 5.4 mmol) is suspended in absolute ethanol (30 mL) previously cooled to −78° C. under argon atmosphere. A solution of the enone (3) obtained in 1.a) (1.0 g, 2.7 mmol) in absolute ethanol (40 mL) is added to the suspension ensuring that the temperature does not exceed −60° C. The reaction is immediately monitored by thin layer chromatography (diethyl ether/ether 1:1); after two hours a 10% (16 mL) citric acid aqueous solution is added to the mixture, which is then diluted with water (50 mL) and extracted with ethyl acetate (3×50 mL). The pooled organic phases are washed with a saturated NaCl solution and dried over anhydrous NaSO$_4$. The solvent is removed under reduced pressure and the product purified by flash chromatography on a silica gel column using as eluant a 8:2 mixture of ethyl ether and petroleum ether. 977 mg (96%) of a white solid are obtained.

1.c) Preparation of methyl (5E,7R,8S)-8-[(tert-butoxycarbonyl)amino]-7-[(tert-butyl-dimethyl-silanyl)oxy]-9-phenyl-non-5-enoate (5)

Tert-butyl-di-methylsilyl chloride (1.65 g, 11 mmol) and imidazole (1.49 g, 22 mmol) are added to a solution of allyl alcohol (4) obtained in 1.b) (1.66 g, 4.4 mmol) in anhydrous dimethylformamide (DMF) (60 mL). After 16 hours of agitation at room temperature, methanol (10 mL) is added and the mixture is agitated for a further 20 minutes. The mixture is diluted with water and extracted with ethyl acetate (3×30 mL). The pooled organic phases are washed with a saturated solution of NaCl and dried over anhydrous Na$_2$SO$_4$. The solvent is removed by distilling under reduced pressure and the crude product is used without any further purification. 1.8 g (85%) of a colourless oil are obtained.

1.d) Preparation of Benzyl (4E,6R,7S)-7-[(Tert-Butoxycarbonyl)Amino]-6-[(tert-butyl-dimethyl-silanyl)oxy]-8-phenyl-oct-4-enylcarbamate (7)

An aqueous solution of lithium hydroxide 0.5N (25 mL) is added to a solution of protected allylic alcohol (5) obtained in 1.c) (1.9 g, 3.8 mmol) in THF (25 mL). After stirring the mixture at room temperature for 16 hours it is acidified to pH 4 with a 10% hydrochloric acid solution then extracted with ethyl ether (3×25 mL). The pooled organic phases are washed with water and a saturated NaCl solution, then dried over anhydrous Na$_2$SO$_4$. The solvent is removed under reduced pressure and the residue (6) (4 mmol) is dissolved in anhydrous toluene (100 mL) to which are added diphenyl phosphoryl azide (1.0 mL, 4.5 mmol) and triethylamine (0.62 mL, 4.5 mmol). The mixture is heated under reflux then after 2 hours benzyl alcohol (0.8 mL, 0.76 mmol) is added and reflux is maintained for 16 hours. After cooling to ambient temperature the solvent is removed by distilling under reduced pressure and the residue partitioned between ethyl acetate and a saturated NaHCO$_3$ solution. The aqueous phase is extracted with ethyl acetate (2×30 mL). The pooled organic phases are washed with a saturated NaCl solution and dried over anhydrous Na$_2$SO$_4$. The solvent is removed under reduced pressure and the residue purified by flash chromatography on a silica gel column using a 4:6 mixture of ethyl acetate/petroleum ether. 1.5 g (68%) of a yellow oil are obtained.

1.e) Preparation of benzyl (4E,6R,7S)-7-[(tert-butoxycarbonyl)amino]-6-hydroxy-8-phenyl-oct-4-enylcarbamate (8)

A 1M solution of tetrabutylammonium fluoride (TBAF) in THF (10.7 mL, 10.7 mmol) is added to a solution of the protected allylic alcohol (7) obtained in 1.d) (1.36 g, 2.34 mmol). The mixture is stirred at room temperature for 16 hours; the solvent is removed under reduced pressure, the residue diluted with water and extracted with ethyl acetate (3×40 mL). The pooled organic phases are washed with a saturated NaCl solution and dried over anhydrous Na$_2$SO$_4$. The solvent is removed under reduced pressure and the product purified by flash chromatography on a silica gel column using ethyl acetate and petroleum ether (gradient from 3:7 to 1:1) as eluant. 930 mg (85%) of a white solid are obtained.

1.f) Preparation of benzyl 3-((2R,3R)-3-{[(1S,2S)-1-hydroxy-2-[(tert-butoxycarbonyl)amino]-3-phenylpropyl}oxiran-2-yl)propylcarbamate (9)

A solution of meta-chloro-perbenzoic acid (mCPBA) (314 mg, 1.1 mmol) in dichloromethane (10 mL) is added to a solution of the allylic alcohol (8) obtained in 1.e) (426 mg, 0.91 mmol) in dichloromethane (10 mL), cooled to 0° C. The mixture is stirred at room temperature for 16 hours, diluted with two volumes of dichloromethane, washed with an 10% aqueous sodium metabisulphite solution (2×25 mL), a saturated NaHCO$_3$ solution (2×25 mL), a saturated NaCl solution then dried over anhydrous Na$_2$SO$_4$. The solvent is removed under reduced pressure and the residue purified by flash chromatography on a silica gel column using an ethyl acetate/dichloromethane mixture as eluent (gradient of 5:5 to 7:3). 300 mg (68%) of a white solid are obtained.

1.g) Preparation of tert-butyl (1S,2S,3S)-1-benzyl-2,3-dihydroxy-3-[(2S)-pyrrolidin-2-yl]propylcarbamate (10)

A solution of the epoxyalcohol (9) obtained in 1.f) (100 mg, 0.26 mmol) in methanol (10 mL) is stirred for 16 hours under hydrogen atmosphere in the presence of 5% Pd/C. The solution is filtered and the solvent removed under reduced pressure. 69 mg (95%) of a white solid are obtained.
P.f.=167° C. $[\alpha]_D^{25}$=−38.8 (c=0.35, MeOH). $^1$H NMR (δ-CDCl$_3$): 1.33 (s, 9H, (C$\underline{H}_3$)$_3$C), 1.57 (m, 1H, C$\underline{H}_2$), 1.76 (m, 2H, C$\underline{H}_2$), 1.91 (m, 1H, C$\underline{H}_2$), 2.86 (m, 1H, C$\underline{H}_2$Ph), 2.92 (m, 1H, C$\underline{H}_2$NH), 2.98 (m, 1H, C$\underline{H}_2$NH), 3.13 (d, 1H, C$\underline{H}_2$Ph, J=13.9 Hz), 3.53-3.66 (m, 3H, 2×C$\underline{H}$OH, C$\underline{H}$NH), 3.91 (bs, 1H, C$\underline{H}$NH), 4.62 (bs, 3H, CHO$\underline{H}$, N$\underline{H}$CO), 7.34 (m, 5H, C$\underline{H}$ Ar). $^{13}$C NMR (δ-CDCl$_3$): 25.16 (C$\underline{H}_2$), 27.30 (C$\underline{H}_2$), 28.32 ((C$\underline{H}_3$)$_3$C), 36.54 (C$\underline{H}_2$Ph), 45.87 (C$\underline{H}_2$NH), 52.78 (C$\underline{H}$NH) 61.90 (C$\underline{H}$NH), 69.64 (C$\underline{H}$OH), 73.05 (C$\underline{H}$OH), 80.15 ((CH$_3$)$_3$$\underline{C}$), 126.45, 128.54, 129.58 (C$\underline{H}$ Ar), 137.92 (C Ar), 157.11 (C$\underline{O}$NH). MS m/z: 351 [MH]$^+$, 295 [MH—C$_4$H$_8$]$^+$.

1.h) Preparation of (1S,2S,3S)-3-amino-4-phenyl-1-[(2S)-pyrrolidin-2-yl]butan-1,2-diol (11)

The diaminodiol tert-butyl (1S,2S,3S)-1-benzyl-2,3-dihydroxy-3-[(2S)-pyrrolidin-2-yl]propylcarbamate (10) obtained in 1.g) (0.15 mmol) is dissolved in a 40% trifluoroacetic acid solution in dichloromethane (1 mL/100 mg of diaminodiol) and the mixture stirred for 1 hour. The solvent is removed by distilling under reduced pressure while excess TFA is removed by co-evaporation with diethyl ether (5×20 mL). The residue is used without further purifications for the subsequent syntheses of the inhibitors.

Example 2

Synthesis of the isostere (1S,2S,3S)-3-amino-4-phenyl-1-[(2S)-pyrrolidin-2-yl]butan-1,2-diol (11)

2.a) Synthesis of N-Cbz-pyrrolidinone

To a solution of 2-pyrrolidinone (1.7 g, 21 mmol) in dry THF (25 mL), at −78° C., a 2.5 N solution of n-buthyllithium in n-hexane (8.4 mL, 21 mmol) is added. The mixture is stirred for 30' and then a solution of benzyl chlorformate (3.03 mL, 21 mmol) in dry THF (30 mL) is added dropwise. The reaction mixture is stirred until the reaction is complete, quenched with saturated aqueous NH$_4$Cl and ectracted with diethyl ether (3×). The combined organic phase is washed with brine and dried over anhydrous Na$_2$SO$_4$. Evaporation of the solvent gives 4 g (87%) of a colourless oil that is used without any further purification.

2.b) Synthesis of N-Cbz-pyrrolidinol

N-Cbz-pyrrolidinone (2.79 g, 0.013 mol), prepared following the procedure described at 1.a), is dissolved in 70 mL of freshly distilled methanol and cooled to 0° C. LiBH$_4$ (707 mg, 0.032 mol) is then added portionwise, the mixture stirred for 20' at 0° C., taken up in ethyl acetate (100 mL), subsequently washed with HCl 1N, brines and the organic phase dried over anhydrous Na$_2$SO$_4$. The solvent is removed under reduced pressure and the residue purified by silica gel chromatography, eluting with a 6/4 dichloromethane/ethyl acetate mixture. The product (2.32 g, 81%) is recovered as a colourless oil.

2.c) Synthesis of (4E,7S)-7-[(tert-butoxycarbonylamino]-6-oxo-8-phenyl-oct-4-enyl)-carbamic acid benzyl ester A solution of N-Cbz-pyrrolidinol (2.3 g, 0.01 mol), prepared in 1.b), in absolute ethanol (50 mL) is added, under stirring, to a solution of ((3S)-3-[(tert-butoxycarbonylamino]-2-oxo-4-phenyl-butyl)-phosphonic acid dimethyl ester) (2) (3.87 g 0.01 mol) and K$_2$CO$_3$ (1.38 g, 0.01 mol), dried at 75° C. for 12 h, in absolute ethanol (80 mL). The mixture is stirred at room temperature for 72 h, the solid residue filtered and the solution neutralized with glacial acetic acid. The solvent is removed under reduced pressure and the residue partitioned between ethyl acetate and saturated aqueous NaHCO$_3$. The aqueous layer is extracted with ethyl acetate (2×50 mL) and the combined organic phase washed with brine and dried over anhydrous Na$_2$SO$_4$. Evaporation of the solvent under reduced pressure and purification of the crude product by silica gel chromatography, eluting with a 1:1 diethyl ether/petroleum ether mixture, afford 2.3 g (50%) of a colourless oil.

2.d) Synthesis of (4E,6R,7S)-7-[(tert-butoxycarbonylamino]-6-hydroxy-8-phenyl-oct-4-enyl)carbamic acid benzyl ester (8)

Tri-tert-butoxy lithium aluminium hydride (980 mg, 3.86 mmol) is suspended in absolute ethanol (30 mL) at −78° C. under argon atmosphere. A solution of the enone obtained in 1.c) (600 mg, 1.29 mmol) in absolute ethanol (40 mL) is added to this suspension, keeping the temperature below −60° C. After 2 h, the mixture is added with a 10% citric acid aqueous solution (16 mL), diluted with water (50 mL) and extracted with ethyl acetate (3×50 mL). The combined organic phase is washed with brine and dried over anhydrous NaSO$_4$. The solvent is removed under reduced pressure and the crude product chromatographed on silica gel (diethyl ether:petroleum ether=8:2), affording 426 mg (70%) of a white solid.

2.e) Preparation of benzyl 3-((2R,3R)-3-{[(1S,2S)-1-hydroxy-2-[(tert-butoxycarbonyl)amino]-3-phenylpropyl}oxiran-2-yl)propylcarbamate (9)

The preparation is as previously described in example 1 step 1.f).

2.f) Preparation of tert-butyl (1S,2S,3S)-1-benzyl-2,3-dihydroxy-3-[(2S)-pyrrolidin-2-yl]propylcarbamate (10)

The preparation is as previously described in example 1 step 1.g).

2.g) Preparation of (1S,2S,3S)-3-amino-4-phenyl-1-[(2S)-pyrrolidin-2-yl]butan-1,2-diol (11)

The preparation is as previously described in example 1 step 1.h).

Example 3

Synthesis of the isostere [(1S,2R,3R)-3-amino-4-phenyl-1-[(2S)-pyrrolidin-2-yl]butan-1,2-diol] (12)

3.a) Preparation of methyl (5E)-6-[(4S,5S)-4-benzyl-2-oxo-1,3-oxazolidin-5-yl]hex-5-enoate (14)

Triethylamine (2.9 mL, 20.7 mmol) and methanesulfonyl chloride (0.8 mL, 10.3 mmol) are added in the stated order to a solution of the allylic alcohol obtained in example (4) 1.b) (2.6 g, 6.9 mmol) in 1,2 dichloroethane (50 mL), cooled to 0° C. The reaction is monitored by thin layer chromatography (diethyl ether). The mixture is stirred at 0° C. until mesylate formation is complete, then maintained at room temperature until the product has completely formed. The solution is diluted with dichloromethane (50 mL) and washed with cold water, a 10% aqueous solution of cold hydrochloric acid, a saturated NaHCO$_3$ solution, a saturated NaCl solution then dried over anhydrous Na$_2$SO$_4$. The solvent is removed under reduced pressure and the product purified by flash chromatography on a silica gel column using diethyl ether as eluant. 1.54 g (74%) of a white solid are obtained.

3.b) Preparation of (4S,5S)-tert-butyl 5-[(E)-5-(methoxycarbonyl)pent-1-enyl]-4-benzyl-2-oxooxazolidin-3-carboxylate (15)

Sodium hydride (60% suspension in mineral oil) is added to a solution of the oxazolidinone (14) obtained in 3.a) (1.4 g, 4.6 mmol) in anhydrous THF (50 mL). The mixture is stirred for 2 hours at room temperature and di-tert-butyl-dicarbonate (1.21 g, 5.5 mmol) is added. The reaction is monitored by thin layer chromatography (diethyl ether) and as soon as it has attained completion a volume of a 10% citric acid solution is added. The mixture is extracted with ethyl acetate (2×50 mL), the pooled organic phases are washed with a saturated NaHCO$_3$ solution and a saturated NaCl solution, then dried over anhydrous Na$_2$SO$_4$. The solvent is removed under reduced pressure and the product used without further purifications.

3.c) Preparation of benzyl methyl (5E,7S,8S)-8-[(tert-butoxycarbonyl)amino]-7-hydroxy-9-phenyl-non-5-enoate (16)

The oxazolidinone (15) obtained in 3.b) (505 mg, 1.25 mmol) is dissolved in a 4:1 mixture of methanol and water (15 mL); $K_2CO_3$ is added (345 mg, 2.5 mol) and the mixture is stirred for 16 hours at room temperature. The solution is neutralized with glacial acetic acid and concentrated to ⅕ of its volume, then extracted with ethyl acetate (2×20 mL). The pooled organic phases are washed with a saturated $NaHCO_3$ solution and a saturated NaCl solution, then dried over anhydrous $Na_2SO_4$. The solvent is removed under reduced pressure and the product purified by flash chromatography on a silica gel column using a 1:1 mixture of ethyl ether and petroleum as eluent. 380 mg (81%) of a white solid are obtained.

3.d) Preparation of benzyl 3-((2S,3S)-3-{[(1R,2S)-1-hydoxy-2-[(tert-butoxycarbonyl)amino]-3-phenylpropyl}oxiran-2-yl)propylcarbamate (17)

880 mg (35%) of a colourless oil are obtained by following the methodology described in 1.c), 1.d), 1.e) and 1.f), starting from the methyl (5E,7S,8S)-8-[(tert-butoxycarbonyl)amino]-7-hydroxy-9-phenyl-non-5-enoate (16) obtained in 3.c) (1.9 g, 5.2 mmol).

3.e) Preparation of benzyl (4R,5R,6R,7S)-4-bromo-7-[(tert-butoxycarbonyl)amino]-5,6-dihydroxy-8-phenyl-octylcarbamate (19)

Amberlist 15 (134 mg, 0.41 mmol) and LiBr (143 mg, 1.65 mmol) are added to a solution of the epoxyalcohol (17) obtained in 3.d) (300 mg, 0.41 mmol) in anhydrous acetonitrile ($CH_3CN$) (4 mL) cooled to −20° C., and the reaction is monitored by thin layer chromatography ($EtOAc/CH_2Cl_2$ 4:6). The mixture is stirred at −20° C. until the reagent has completely disappeared, the solid is removed by filtration and the solvent removed under reduced pressure. The residue is re-dissolved in ethyl acetate (25 mL) and the organic phase is washed with water (10 mL) and a saturated NaCl solution, then dried over anhydrous $NaSO_4$. The solvent is removed under reduced pressure and the residue is purified by flash chromatography on a silica gel column using a 1:1 mixture of ethyl acetate/dichloromethane as eluent. 127 mg (55%) of an oil are obtained.

3.f) Preparation of tert-butyl (1S,2R,3R)-1-benzyl-2,3-dihydroxy-3-[(2S)-pyrrolidin-2-iy]propylcarbamate (20)

A solution of the bromodiol (19) obtained in 3.e) (127 mg, 0.22 mmol) is stirred for 2 hours under hydrogen atmosphere in the presence of a catalytic quantity of 5% Pd/C. The mixture is filtered through celite and di-iso-propylethylamine (38 μL, 0.22 mmol) added. The solution is stirred for 16 hours and the solvent removed under reduced pressure. The residue is partitioned between ethyl acetate and water, the organic phase is washed with a saturated NaCl solution then dried over $NaSO_4$. 59 mg (75%) of a colourless oil are obtained.

$[\alpha]_D^{25}$=−14.3 (c=0.28, MeOH). $^1$H NMR (δ-$CD_3OD$): 1.33 (s, 9H, $(C\underline{H}_3)_3C$), 1.57 (m, 1H, $C\underline{H}_2$), 1.78 (m, 2H, $C\underline{H}_2$), 1.91 (m, 1H, $C\underline{H}_2$), 2.78-2.90 (m, 4H, $C\underline{H}_2Ph$ e $C\underline{H}_2NH$), 3.65-3.82 (m, 3H, 2×$C\underline{H}OH$, $C\underline{H}NH$), 4.06 (m, 1H, $C\underline{H}NH$), 7.34 (m, 5H, $C\underline{H}$ Ar). $^{13}$C NMR (δ-$CD_3OD$): 24.29 ($\underline{C}H_2$ ring), 25.42 ($\underline{C}H_2$ ring), 28.39 (($\underline{C}H_3)_3C$), 39.28 ($\underline{C}H_2Ph$), 45.56 ($\underline{C}H_2NH$), 53.25 ($\underline{C}HNH$) 60.63 ($\underline{C}HNH$), 74.14 ($\underline{C}HOH$), 77.36 ($\underline{C}HOH$), 80.20 (($CH_3)_3\underline{C}$), 126.45, 128.54, 129.46 ($\underline{C}H$ Ar), 137.95 ($\underline{C}$ Ar), 158.01 ($\underline{C}ONH$). MS m/z: 351 $[MH]^+$, 373 $[MNa]^+$.

Example 4

Synthesis of the isostere [(1S,2R,3R)-3-amino-4-phenyl-1-[(2S)-pyrrolidin-2-yl]butan-1,2-diol] (12)

4.a) Synthesis of (4E,6S,7S)-7-[(tert-butoxycarbonylamino]-6-hydroxy-8-phenyl-oct-4-enyl)carbamic acid benzyl ester To a solution of the enone (1.0 g, 2.14 mmol), obtained in 1.c) of the example 2, in 30 mL of freshly distilled methanol, at −78° C. and under argon atmosphere, L-Selectride 1.0 M in THF (6.42 mL) is added. After 3 h, the solution is acidified to pH 5 with HCl 1N and the solvent removed under reduced pressure. The residue is rinsed with ethyl acetate and saturated aqueous $NaHCO_3$ and the aqueous layer repeatedly extracted with ethyl acetate (3×30 mL). The combined organic phase is then washed with brine, dried over anhydrous $Na_2SO_4$, the solvent removed under reduced pressure and the residue purified by silica gel chromatography eluting with a petroleum ether/ethyl acetate mixture (gradient from 8/2 to 1/1), recovering 600 mg (60%) of a white solid.

4.b) Preparation of benzyl 3-((2S,3S)-3-{[(1R,2S)-1-hydoxy-2-[(tert-butoxycarbonyl)amino]-3-phenylpropyl}oxiran-2-yl)propylcarbamate (17)

The preparation is as previously reported in example 3 step 3.d).

4.c) Preparation of benzyl (4R,5R,6R,7S)-4-bromo-7-[(tert-butoxycarbonyl)amino]-5,6-dihydroxy-8-phenyl-octylcarbamate (19)

The preparation is as previously reported in example 3 step 3.e).

4.d) Preparation of tert-butyl (1S,2R,3R)-1-benzyl-2,3-dihydroxy-3-[(2S)-pyrrolidin-2-iy]propylcarbamate (20)

The preparation is as previously reported in example 3 step 3.f).

Example 5

Synthesis of the isostere (1S,2R,3R)-3-amino-4-phenyl-1-((R)-pyrrolidin-2-yl)butan-1,2-diol (13)

64 mg (89%) of a colourless oil are obtained by following the methodology described in 1.g) starting from the benzyl 3-((2S,3S)-3-{[(1R,2S)-1-hydroxy-2-[(tert-butoxycarbonyl)amino]-3-phenylpropyl}oxiran-2-yl)propylcarbamate (17) (100 mg, 2.06 mmol) obtained in 3.d) or 4.b).

$^1$H NMR (δ-$CDCl_3$): 1.35 (s, 9H, (($C\underline{H}_3)_3C$), 1.56 (m, 1H, $C\underline{H}_2$), 1.85 (m, 2H, $C\underline{H}_2$ ring), 2.02 (m, 1H, $C\underline{H}_2$), 2.73-3.12 (m, 7H, $C\underline{H}_2Ph$ β, $C\underline{H}_2NH$, 2×$C\underline{H}OH$, $C\underline{H}NH$), 4.38 (bs, 2H, O$\underline{H}$), 4.56 (d, 1H, N$\underline{H}$, J=7.9 Hz), 4.85 (m, 1H, $C\underline{H}N$), 7.12-

7.27 (m, 5H, C$\underline{H}$ Ar). $^{13}$C NMR (δ-CDCl$_3$): 22.43 (C$\underline{H}_2$), 28.25 (C$\underline{H}_2$), 28.51 ((C$\underline{H}_3$)$_3$C), 35.37 (C$\underline{H}_2$Ph), 47.88 (C$\underline{H}_2$NH), 55.19 (C$\underline{H}$NH) 62.89 (C$\underline{H}$NH), 75.32 (C$\underline{H}$OH), 79.71 (C$\underline{H}$OH), 82.15 ((CH$_3$)$_3$$\underline{C}$), 126.40, 126.51, 128.13, 128.44, 128.55, 129.25, (C$\underline{H}$ Ar), 138.09, 140.13 (C Ar), 158.59 (C$\underline{O}$NH). MS m/z: 441 [MH]$^+$, 464 [MNa]$^+$.

Example 6

Synthesis of the Inhibitor NH-Ac-Trp-Val-Phe-[φ]-Pro-Val-Trp-NH-Ac (22)

Benzotriazole-1-yl-oxy-tris-pyrrolidino-phosphonium hexafluorophosphate (PYBOP®) (249 mg, 0.48 mmol), HOBT (65 mg, 0.48 mmol), collidine (0.13 mL, 0.96 mmol) and the diaminodiol (1S,2S,3S)-3-amino-4-phenyl-1-[(2S)-pyrrolidin-2-yl]butan-1,2-diol (11) obtained from example 1 (30 mg, 0.12 mmol) are added to a solution of the acetylated dipeptide AcNH-Trp-Val-OH (165 mg, 0.48 mmol) in anhydrous DMF (1 mL) and the mixture is stirred for 48 hours. The solvent is removed under reduced pressure and the residue partitioned between ethyl acetate (40 mL) and water (15 mL). The organic phase is washed with a 5% aqueous KHSO$_4$ (2×15 mL) solution and a saturated NaCl solution then dried over anhydrous NaSO$_4$. The solvent is removed under reduced pressure and the crude product is purified by flash chromatography on a silica gel column using a 9:1 dichloromethane/methanol mixture as eluant. 54 mg (50%) of a white solid are obtained.

MS m/z: 906 [MH]$^+$, 928 [MNa]$^+$, 944 [MK]$^+$.

Example 7

Synthesis of the Inhibitor NH-Ac-Ser-Leu-Asn-Phe-[φ]-Pro-Ile-Val-NH-Ac (21)

In the stated order, PYBOP® (145 mg, 028 mmol), HOBT (38 mg, 028 mmol), collidine (63 μL, 0.47 mmol) and diaminodiol tert-butyl (1S,2S,3S)-1-benzyl-2,3-dihydroxy-3-[(2S)-pyrrolidin-2-yl]propylcarbamate (10) obtained in 1.g) (50 mg, 0.14 mmol) are added to a solution of the acetylated dipeptide Ac-NH-Val-Ile-OH (78 mg, 0.28 mmol) in anhydrous DMF (1 mL). After 72 hours the mixture is treated as described in example 6 and the crude product thus obtained is deprotected from Boc by treating with TFA as described in 1.h). The deprotected peptide (91 mg, 0.18 mmol) is dissolved in anhydrous DMF (0.5 mL) and added to a solution of the acetylated, and protected as benzyl ether at the hydroxy group of the serine, tripeptide Ac-NH-Ser(OBz)-Leu-Asn-OH (120 mg, 0.27 mmol), PyBOP® (140 mg, 0.27 mmol), HOBT (36 mg, 0.26 mmol) and collidine (71 μL, 0.54 mmol). The mixture is stirred for 72 hours and the product is isolated by following the procedure described in example 6. The benzylic protection of the hydroxyl is removed by catalytic hydrogenation: a catalytic quantity of 10% Pd/C is added to the residue, dissolved in methanol (10 mL), and the mixture is stirred under H$_2$ atmosphere for 48 hours. The solution is filtered through celite and the solvent removed under reduced pressure. The crude product is purified by flash chromatography on a silica gel column using a 9:1 dichloromethane/methanol mixture as eluant. 26.5 mg (12%) of a colourless oil are obtained.

MS m/z: 861 [MH]$^+$, 883 [MNa]$^+$, 899 [MK]$^+$.

Example 8

Synthesis of the Inhibitor DmPoa-Phe-[φ]-Pro-DmPoa (23)

The inhibitor is synthesized following the procedure of example 6 starting from 2,6-dimethyl-phenoxyacetic acid (DmPoa) (50 mg, 0.28 mmol), HOBT (38 mg, 0.28 mmol), N-methyl morpholine (NMM) (0.92 mL, 0.28 mmol), EDC (56 mg, 0.29 mmol) and the diaminodiol (1S,2S,3S)-3-amino-4-phenyl-1-[(2S)-pyrrolidin-2-yl]butan-1,2-diol (11) of example 1 (35 mg. 0.14 mmol). 96 mg (60%) of a white solid are obtained.

$^{13}$C NMR (δ-CD$_3$CN): 16.25 (C$\underline{H}_3$), 16.50 (C$\underline{H}_3$), 23.86 (C$\underline{H}_2$), 27.66 (C$\underline{H}_2$), 37.81 (C$\underline{H}_2$Ph), 46.83 (C$\underline{H}_2$N), 52.60 (C$\underline{H}$NH), 59.82 (C$\underline{H}$NH), 70.82 (C$\underline{H}$OH), 71.00 (C$\underline{H}_2$O), 71.38 (C$\underline{H}$OH), 71.75 (C$\underline{H}_2$OH), 125.25, 125.61 (C Ar), 127.21, 129.29, 129.85, 129.90, 130.40, 131.64, 131.82 (C$\underline{H}$ Ar), 139.86, 155.24, 156.73 (C Ar), 170.12, 170.46 (C$\underline{O}$NH). MS m/z: 575 [MH]$^+$, 597 [MNa]$^+$.

Example 9

Synthesis of the Inhibitor DmPoa-Phe-[φ]-Pro-Poa (25)

In this order, HOBT (19 mg, 0.14 mmol), EDC (28 mg, 0.15 mmol), NMM (31 μl, 0.28 mmol) and diaminodiol tert-butyl (1S,2S,3S)-1-benzyl-2,3-dihydroxy-3-[(2S)-pyrrolidin-2-yl]propylcarbamate (10) of example 1.g) (50 mg, 0.14 mmol) are added to a solution of phenoxyacetic acid (POA) (22 mg, 0.14 mmol) in anhydrous DMF (1 mL). The mixture is stirred for 16 hours and the product isolated by following the procedure described in example 6. The crude product is deprotected from the Boc by treating with TFA as described in 1.h). The residue (49 mg, 0.13 mmol) is dissolved in anhydrous DMF (0.5 mL) and added to a solution of 2,6-dimethyl-phenoxyacetic acid (DmPoa) (25 mg, 0.14 mmol), HOBT (19 mg, 0.14 mmol), EDC (28 mg, 0.15 mmol), NMM (31 μL, 0.28 mmol). The mixture is agitated for 16 hours and the product is isolated by following the procedure of example 6. The crude product is purified by flash chromatography on a silica gel column using a 9:1 dichloromethane/methanol mixture as eluant. 18 mg (24%) of a white solid are obtained.

$^1$H NMR (δ-CDCl$_3$): 1.90 (m, 3H, C$\underline{H}_2$ e $\underline{H}$CH), 2.06 (s, 6H, 2×C$\underline{H}_3$), 2.27 (m, 1H, HC$\underline{H}$), 2.86 (dd, 1H, C$\underline{H}_2$Ph, J$_1$=8.8 Hz, J$_2$=14.3 Hz), 3.15 (dd, 1H, C$\underline{H}_2$, J$_1$=5.1 Hz, J$_2$=9.1 Hz), 3.20 (dd, 1H, C$\underline{H}_2$, J$_1$=6.9 Hz, J$_2$=9.1 Hz), 3.32 (dd, 1H, C$\underline{H}_2$Ph, J$_1$=8.8 Hz, J$_2$=14.3 Hz), 3.48 (m, 2H, C$\underline{H}$OH), 3.93 (d, 1H, O$\underline{H}$, J=6.2 Hz), 4.11 (dd, 2H, C$\underline{H}_2$O, J$_1$=15.4 Hz, J$_2$=24.5 Hz), 4.36 (m, 2H, C$\underline{H}$NH), 4.65 (dd, 2H, C$\underline{H}_2$O, J$_1$=14.6 Hz, J$_2$=19.04 Hz), 4.83 (d, 1H, O$\underline{H}$, J=4.7 Hz), 6.72 (d, 1H, N$\underline{H}$, J=9.1 Hz), 6.97 (m, 7H, C$\underline{H}$ Ar e N$\underline{H}$), 7.25 (m, 7H, C$\underline{H}$ Ar). $^{13}$C NMR (δ-CDCl$_3$): 15.91 (C$\underline{H}_3$), 16.06 (C$\underline{H}_3$), 23.55 (C$\underline{H}_2$), 26.93 (C$\underline{H}_2$), 37.14 (C$\underline{H}_2$Ph), 46.70 (C$\underline{H}_2$NH), 51.01 (C$\underline{H}$NH), 59.01 (C$\underline{H}$NH), 67.50 (C$\underline{H}_2$O), 69.85 (C$\underline{H}_2$O), 70.10 (C$\underline{H}$OH), 70.93 (C$\underline{H}$OH), 121.82, 124.84, (C Ar), 126.62, 128.60, 129.05, 129.12, 129.30, 129.37, 129.62, 129.69, 130.25 (CHAr), 137.65 (CAr), 153.92, 157.62 (CO), 169.45, 169.75 (CONH). MS m/z: 546 [MH]⁺, 585 [MNa]⁺, 569 [MK]⁺.

Example 10

Synthesis of the Inhibitor
DmPoa-Phe-[φ]-Pro-Val-Trp-NH-Ac (24)

This inhibitor was synthesized by introducing the amino acids in a side chain one after the other in the stated order: N-Cbz-valine, Ac-NH-tryptophan, DmPoa. 104 mg (78%) of a white solid are obtained by following the method described in example 6, starting from 2,6-dimethyl-phenoxyacetic acid (DmPoa) (25 mg, 0.14 mmol), N-Cbz-valine (41.6 mg, 0.18 mol), NH-Ac-tryptophan (39 mg, 0.15 mmol), and diamino tert-butyl (1S,2S,3S)-1-benzyl-2,3-dihydroxy-3-[(2S)-pyrrolidin-2-yl]propylcarbamate (10) of example 1.g) (62 mg, 0.18 mmol).

MS m/z: 740 [MH]⁺, 762 [MNa]⁺, 778 [MK]⁺.

Biological Activity: Inhibition of the HIV-Protease In Vitro

Inhibitory activity was measured in accordance with the method described by A. Tossi et al. (*Eur. J. Biochem.*, 2000, 267, 1715) using an HIV-1 recombinant protease supplied by Bioczech (Prague, CZ) and the fluorogenic substrate Abz-Thr-Ile-Nle-Phe(p-NO$_2$)-Gln-Arg-NH$_2$ (abbreviated hereinafter as Abz-NF*-6) supplied by Bachem (Bubendorf, CH). Specifically, 189 µL of a 30 µM solution of Abz-NF*-6 in a 100 mM MES-NaOH buffer (pH 5.5) containing NaCl (400 mM), EDTA (1 mM), DTT (1 mM) and BSA (1 mg/mL) are incubated at 25° C. in a cuvette placed directly in the spectrofluorimeter, irradiated at 325 mn and checking that there is no increase of emission at 420 nm due to the spontaneous hydrolysis of the substrate. After 1.5 minutes 11 µL of a standard solution of HIV-PR (0.4 mg/mL) in the same buffer are added and the variation in fluorescence, due to catalysed hydrolysis of the Abz-NF*-6 substrate, is recorded for 1 minute. 2 µL of the inhibitor solution in DMSO or MES buffer are then added and the variation in fluorescence over time due to hydrolysis of the Abz-NF*-6 substrate in the presence of the specific inhibitor is recorded. This measurement was taken at 7 different inhibitor concentrations for each of the inhibitors synthesized in examples 6-10, as shown in table 1:

The IC$_{50}$ values (defined as inhibitor concentration needed to reduce enzyme activity by 50%) obtained for the inhibitors of examples 6 to 10 are summarized in table 2.

TABLE 2

| | IC$_{50}$ HIV-protease inhibitors | |
|---|---|---|
| Inhibitor | IC$_{50}$ nM | MW |
| (21) | 0.61 | 860 |
| (22) | 0.06 | 905 |
| (23) | 9.6 | 574 |
| (24) | 75.3 | 739 |
| (25) | 84.7 | 545 |

Regarding the specific biological activities of HIV-protease inhibition, the inhibitors of the invention can be usefully employed as antivirals in infections from retroviral agents and in particular in acquired immunodeficiency syndrome from HIV. The inhibitors can be used both as post exposure prophylaxis or as infection therapy in accordance with prophylactic or therapeutics regimens as chosen by the physician based on the clinical status of the patient. For the aforecited therapeutic or prophylactic purposes the inhibitors of the invention can be administered in compositions with pharmaceutically acceptable excipients and diluents, also in slow release compositions and known pharmaceutical forms suited for the purpose. Without excluding other administration routes, the inhibitors of the invention can be administered orally or parenterally; for oral administration suitable compositions can be in the form of dispersible powders, tablets, pills, soft or hard gelatin capsules, suspensions, emulsions and solutions, while for parenteral, intramuscular, subcutaneous and intravenous administration suitable compositions can be in the form of buffered aqueous solutions, oily suspensions or lyophilized powders to be dispersed in a suitable solvent at the moment of administration.

The invention claimed is:

1. A HIV protease inhibitor of general formula (I),

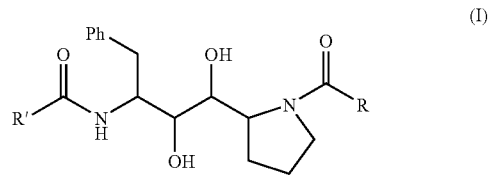

(I)

TABLE 1

| | concentrations of HIV-protease inhibitors | | | | | | |
|---|---|---|---|---|---|---|---|
| Inhibitor | Dil. 1 DMSO (M) | Dil. 2 DMSO (M) | Dil. 3 MES (M) | Dil. 4 MES (M) | Dil. 5 MES (M) | Dil. 6 MES (M) | Dil. 7 MES (M) |
| (21) | $2.5 \cdot 10^{-3}$ | $1.25 \cdot 10^{-3}$ | $5 \cdot 10^{-5}$ | $5 \cdot 10^{-7}$ | $5 \cdot 10^{-8}$ | $2.5 \cdot 10^{-8}$ | $5 \cdot 10^{-9}$ |
| (22) | $2.5 \cdot 10^{-3}$ | $1.25 \cdot 10^{-3}$ | $5 \cdot 10^{-5}$ | $5 \cdot 10^{-7}$ | $5 \cdot 10^{-8}$ | $5 \cdot 10^{-8}$ | $5 \cdot 10^{-10}$ |
| (23) | $5 \cdot 10^{-3}$ | $2.5 \cdot 10^{-3}$ | $1 \cdot 10^{-4}$ | $1 \cdot 10^{-5}$ | $1 \cdot 10^{-6}$ | $1 \cdot 10^{-7}$ | $1 \cdot 10^{-8}$ |
| (24) | $1.95 \cdot 10^{-3}$ | $9.7 \cdot 10^{-4}$ | $4 \cdot 10^{-4}$ | $2.43 \cdot 10^{-4}$ | $2.4 \cdot 10^{-8}$ | $2.4 \cdot 10^{-9}$ | $2.4 \cdot 10^{-10}$ |
| (25) | $5 \cdot 10^{-3}$ | $2.5 \cdot 10^{-3}$ | $1.25 \cdot 10^{-3}$ | $6.25 \cdot 10^{-4}$ | $3.1 \cdot 10^{-4}$ | $3.12 \cdot 10^{-5}$ | $3.12 \cdot 10^{-6}$ | and pharmaceutically acceptable salts or esters thereof wherein R and R' can be independently one from the other selected from the group consisting of amino acids; peptide chains with two or three amino acids selected from the group consisting of Valine, Leucine, Isoleucine, Thienylglycine, Asparagine, Tryptophan, Phenylalanine, Cyclohexilalanine, Serine, and Threonine; and carboxylic acids, and wherein the carboxylic acids are selected from the group consisting of phenoxyacetic acid and kynurenic acid substituted with methyl groups.

2. A HIV protease inhibitor as claimed in claim 1 selected from the group consisting of the inhibitor NH-Ac-Trp-Val-Phe-[φ]-Pro-Val-Trp-NH-Ac, the inhibitor NH-Ac-Ser-Leu-Asn-Phe-[φ]-Pro-Ile-Val-NH Ac, the inhibitor DmPoa-Phe-[φ]-Pro-DmPoa, the inhibitor DmPoa-Phe-[φ]-Pro-Poa, and the inhibitor DmPoa-Phe-[φ]-Pro-Val-Trp-NH-Ac.

* * * * *